United States Patent
Aminifar et al.

(10) Patent No.: US 12,419,566 B2
(45) Date of Patent: Sep. 23, 2025

(54) WEARABLE SYSTEM FOR REAL-TIME DETECTION OF EPILEPTIC SEIZURES

(71) Applicant: ECOLE POLYTECHNIQUE FEDERALE DE LAUSANNE (EPFL), Lausanne (CH)

(72) Inventors: Amir Aminifar, Lausanne (CH); Dionisije Sopic, Lausanne (CH); David Atienza Alonso, Echandens-Denges (CH); Renato Zanetti, Lausanne (CH)

(73) Assignee: ECOLE POLYTECHNIQUE FÉDÉRALE DE LAUSANNE (EPFL), Lausanne (CH)

( * ) Notice: Subject to any disclaimer, the term of this patent is extended or adjusted under 35 U.S.C. 154(b) by 365 days.

(21) Appl. No.: 16/970,858

(22) PCT Filed: Feb. 20, 2019

(86) PCT No.: PCT/IB2019/051377
§ 371 (c)(1),
(2) Date: Aug. 18, 2020

(87) PCT Pub. No.: WO2019/162850
PCT Pub. Date: Aug. 29, 2019

(65) Prior Publication Data
US 2020/0375524 A1 Dec. 3, 2020

(30) Foreign Application Priority Data

Feb. 20, 2018 (WO) .................. PCT/IB2018/051032

(51) Int. Cl.
*A61B 5/00* (2006.01)
*A61B 5/291* (2021.01)

(52) U.S. Cl.
CPC .......... *A61B 5/4094* (2013.01); *A61B 5/0006* (2013.01); *A61B 5/291* (2021.01); *A61B 5/6814* (2013.01); *A61B 5/7264* (2013.01)

(58) Field of Classification Search
CPC ..... A61B 5/4094; A61B 5/291; A61B 5/0006; A61B 5/6814; A61B 5/7264
(Continued)

(56) References Cited

U.S. PATENT DOCUMENTS 7,299,088 B1 * 11/2007 Thakor ................ A61B 5/4094
600/544
2009/0124923 A1 * 5/2009 Sackellares .......... A61B 5/7275
600/544

(Continued)

FOREIGN PATENT DOCUMENTS

KR  10-2015-0061766  6/2015
KR  2015-0061766 A  6/2015

OTHER PUBLICATIONS

Grayson, "Giganti.Co Waveguides + Eye-Tracking + EEG", Oct. 24, 2016, Retrieved from the Internet: URL: http://www.giganti.co/EyeTrackingEEG, 10 pages.
(Continued)

*Primary Examiner* — Alex M Valvis
*Assistant Examiner* — Jonathan M Haney
(74) *Attorney, Agent, or Firm* — Nixon & Vanderhye P.C.

(57) ABSTRACT

A wearable system for epileptic seizure detection, comprising an eyeglasses frame, with a left arm and a right arm configured to rest over the ears of an intended person wearing the eyeglasses, a first pair of electrodes located in the left arm, and a second pair of electrodes located in the right arm, the first pair of electrodes and the second pair of electrodes arranged such to be in contact with the skull of the intended person wearing the eyeglasses, and an EEG signal
(Continued)

acquiring system integral to the left and right arms, connected to measuring outputs of the respective first pair and second pair of electrodes.

11 Claims, 6 Drawing Sheets

(58) Field of Classification Search
USPC .................................................. 600/544–545
See application file for complete search history.

(56) References Cited

U.S. PATENT DOCUMENTS

| | | | |
|---|---|---|---|
| 2011/0270117 A1* | 11/2011 | Warwick | A61B 5/0006 600/544 |
| 2017/0188947 A1* | 7/2017 | Connor | A61B 5/369 |
| 2017/0258410 A1 | 9/2017 | Gras | |

OTHER PUBLICATIONS

Bose et al., "EEG signal analysis for Seizure detection using Discrete Wavelet Transform and Random Forest", 2017 International Conference on Computer and Applications (ICCA), IEEE, Sep. 6, 2017, pp. 369-378.
Mursalin et al., "Automated epileptic seizure detection using improved correlation-based feature selection with random forest classifier", Neurocomputing, vol. 241, Feb. 23, 2017, pp. 204-214.
Wang et al., "Automatic Epileptic Seizure Detection in EEG Signals Using Multi-Domain Feature Extraction and Nonlinear Analysis", Entropy, vol. 19, No. 6, May 27, 2017, 17 pages.
Sopic et al., "Real-Time Classification Technique for Early Detection and Prevention of Myocardial Infarction on Wearable Devices", 2017 IEEE Biomedical Circuits And Systems Conference (BIOCAS), IEEE, Oct. 19, 2017, 4 pages.
International Search Report for PCT/IB2019/051377 mailed Jun. 5, 2019, 5 pages.
Written Opinion of the ISA for PCT/IB2019/051377 mailed Jun. 5, 2019, 7 pages.
Acharya, U. Rajendra, et al., "Application of entropies for automated diagnosis of epilepsy using EEG signals: A review," Knowledge-Based Systems, vol. 88, 2015, pp. 85-96.
Bandt, Christoph, et al., "Permutation Entropy: A Natural Complexity Measure for Time Series," Physical Review Letters, vol. 88, No. 17, Apr. 29, 2002, pp. 174102-1-174102-4.
Bareket, Lilach, et al., "Temporary-tattoo for long-term high fidelity biopotential recordings," Scientific Reports, vol. 6, 2016, 8 pages.
Bell, Martha Ann, et al., "Using EEG to Study Cognitive Development: Issues and Practices," Journal of Cognition and Development, vol. 13, No. 3, Jul. 2012, pp. 281-294.
Bellotti, R., et al., "Migraine detection through spontaneous EEG analysis," Proceedings of the 29th Annual International Conference of the IEEE EMBS, 2007, pp. 1834-1837.
Blom, J. L., et al., "An Electrode Cap Tested," Electroencephalography and clinical Neurophysiology, vol. 54, No. 5, Nov. 1982, pp. 591-594.
Blumenfeld, Hal, "Impaired Consciousness in Epilepsy," The Lancet Neurology, vol. 11, No. 9, Sep. 2012, pp. 814-826.
Boostani, Reza, et al., "A comparative review on sleep stage classification methods in patients and healthy Individuals," Computer Methods and Programs in Biomedicine, vol. 140, 2017, pp. 77-91.
Cascino, Gregory D., "Video-EEG Monitoring in Adults," Epilepsia, vol. 43, Suppl. 3, 2002, pp. 80-93.
Chen, Xinnian, et al., "Comparison of the Use of Approximate Entropy and Sample Entropy: Applications to Neural Respiratory Signal," Proceedings of the 2005 IEEE Engineering in Medicine and Biology 27th Annual Conference, vol. 4, 2005, pp. 4212-4215.

Chen, Yun-Hsuan, et al., "Soft, Comfortable Polymer Dry Electrodes for High Quality ECG and EEG Recording," Sensors, vol. 14, 2014, pp. 23758-23780.
Coben, Lawrence A., et al., "A Longitudinal EEG Study of Mild Senile Dementia of Alzheimer Type: Changes at 1 Year and at 2.5 Years," Electroencephalography and clinical Neurophysiology, vol. 61, No. 2, 1985, pp. 101-112.
Daly, Janis J. et al., "Brain-computer interfaces in neurological rehabilitation," The Lancet Neurology, vol. 7, No. 11, Nov. 2008, pp. 1032-1043.
Díaz-Uriarte, Ramón, et al., "Gene selection and classification of microarray data using random forest," BMC Bioinformatics, vol. 7, No. 3, 2006, 13 pages.
Dijk, Derk Jan, et al., "Sex Differences in the Sleep EEG of Young Adults: Visual Scoring and Spectral Analysis," Sleep, vol. 12, No. 6, 1989, pp. 500-507.
Dunn-Henriksen, Jonas, et al., "EEG Signal Quality of a Subcutaneous Recording System Compared to Standard Surface Electrodes," Journal of Sensors, vol. 2015, Article ID 341208, 2015, 9 pages.
Fürbass, F., et al., "Automatic multimodal detection for long-term seizure documentation in epilepsy," Clinical Neurophysiology, vol. 128, No. 8, Aug. 2017, pp. 1466-1472.
Goldberger, Ary L., et al., "PhysioBank, PhysioToolkit, and PhysioNet Components of a New Research Resource for Complex Physiologic Signals," Circulation, vol. 101, No. 23, Jun. 2000, 6 pages.
Hirtz, D., et al., "How common are the "common" neurologic disorders?", Neurology, vol. 68, No. 5, Jan. 2007, pp. 326-337.
Hoppe, Christian, et al., "Novel techniques for automated seizure registration: Patients' wants and needs," Epilepsy & Behavior, vol. 52, Pt. A, Nov. 2015, pp. 1-7.
Hosseini, Seyyed Abed, et al., "Emotional stress recognition system using EEG and psychophysiological signals: Using new labelling process of EEG signals in emotional stress state," IEEE, 2010, 6 pages.
Jeong, Jaeseung, "EEG dynamics in patents with Alzheimer's disease," Clinical Neurophysiology, vol. 115, No. 7, 2004, pp. 1490-1505.
Jordan, Kenneth G., "Emergency EEG and Continuous EEG Monitoring in Acute Ischemic Stroke," Journal of Clinical Neurophysiology, vol. 21, No. 5, Oct. 2004, pp. 341-352.
Kim, K. H., et al., "Emotion recognition system using short-term monitoring of physiological signals," Medical & Biological Engineering & Computing, vol. 42, 2004, pp. 419-427.
Klem, George H., et al., "The ten-twenty electrode system of the International Federation," Recommendations for the Practice of Clinical Neurophysiology: Guidelines of the International Federation of Clinical Physiology, EEG Suppl. 52, Chapter 1.1, 1999, pp. 3-6.
Kwan, Patrick, et al., "Definition of refractory epilepsy: defining the indefinable?", The Lancet Neurology, vol. 9, No. 1, Jan. 2010, pp. 27-29.
Liaw, Andy, et al., "Classification and Regression by randomForest," R News, vol. 2/3, Dec. 2002, pp. 18-22.
Lin, Yuan-Pin, et al., "EEG-Based Emotion Recognition in Music Listening," IEEE Transactions on Biomedical Engineering, vol. 57, No. 7, Jul. 2010, pp. 1798-1806.
O'Dwyer, Rebecca, et al., "Lateralizing Significance of Quantitative Analysis of Head Movements before Secondary Generalization of Seizures of Patients with Temporal Lobe Epilepsy," Epilepsia, vol. 48, No. 3, 2007, pp. 524-530.
Ocak, Hasan, "Automatic detection of epileptic seizures in EEG using discrete wavelet transform and approximate entropy," Expert Systems with Applications, vol. 36, No. 2, Mar. 2009, pp. 2027-2036.
Ramgopal, Sriram, et al., "Seizure detection, seizure prediction, and closed-loop warning systems in epilepsy," Epilepsy & Behavior, vol. 37, 2014, pp. 291-307.
Ryvlin, Philippe, et al., "Surmortalite et mort soudaine inattendue dans l'épilepsie [Excess mortality and sudden unexpected death in epilepsy]," Presse Medicale, vol. 38, No. 6, Jun. 2009, pp. 905-910.

(56) References Cited

OTHER PUBLICATIONS

Setz, Cornelia, et al., "Discriminating Stress From Cognitive Load Using a Wearable EDA Device," IEEE Transactions on Information Technology in Biomedicine, vol. 14, No. 2, Mar. 2010, pp. 410-417.
Sharma, Aarti, "Epileptic Seizure Prediction using Power Analysis in Beta Band of EEG Signals," 2015 International Conference on Soft Computing Techniques and Implementations (ICSCTI), IEEE, Oct. 2015, pp. 117-121.
Sopic, Dionisije, et al., "Real-Time Event-Driven Classification Technique for Early Detection and Prevention of Myocardial Infarction on Wearable Systems," IEEE Transactions on Biomedical Circuits and Systems, vol. 12, No. 5, Oct. 2018, pp. 982-992.
Stauffer, Flurin, et al., "Skin Conformal Polymer Electrodes for Clinical ECG and EEG Recordings," Advanced Healthcare Materials, vol. 7, 2018, 10 pages.
Szucs, A., et al., "Sudden death and mortality in epilepsy," Ideggyogyaszati Szemle, vol. 59, No. 9-10, Sep. 2006, pp. 321-328.
Webster, John G. (Editor), "Medical Instrumentation: Application and Design," Wiley, 2008.
"10/20 System Electrode Distances," DIY tDCS, posted on Jul. 22, 2012, 2 pages, retrieved Sep. 7, 2020, https://www.diytdcs.com/2012/07/1020-system-electrode-distances/.
"A closer look at EEG," Epilepsy Society, 14 pages, retrieved Sep. 7, 2020, https://www.epilepsysociety.org.uk/closer-look-eeg#.WhE8o7aZPxg.
"About Epilepsy: The Basics," Epilepsy Foundation, 3 pages, retrieved Sep. 7, 2020, https://www.epilepsy.com/learn/about-epilepsy-basics.
"EEG Games Top 5 List: Playing with Your Brainwaves," "The MindWave Headset: Making EEG Games Possible," NeuroSky, Sep. 21, 2015, 3 pages, retrieved Sep. 7, 2020, http://neurosky.com/2015/09/eeg-games-top-5-list-playing-with-your-brainwaves/.
STM32L Series Datasheet—Production Data, STMicroelectronics, Oct. 2017, 134 pages.

* cited by examiner

WEARABLE SYSTEM FOR REAL-TIME DETECTION OF EPILEPTIC SEIZURES

This application is the U.S. national phase of International Application No. PCT/IB2019/051377 filed Feb. 20, 2019 which designated the U.S. and claims priority to International Application No. PCT/IB2018/051032 filed Feb. 20, 2018, the entire contents of each of which are hereby incorporated by reference.

FIELD OF INVENTION

The invention is in the field of non-invasive epilepsy monitoring.

BACKGROUND

Epilepsy represents one of the major neurological health issues affecting more than 65 million people worldwide [1]. It is the fourth most common chronic disorder after migraine, stroke, and Alzheimer's disease [2], with a higher prevalence in children. Despite substantial progress in the efficacy and tolerance of anti-epileptic drugs, one third of these patients continue to have seizures [3].

Epilepsy is characterized by intermittent seizures caused by disturbances in the electrical activity of the brain [1]. These seizures can last from seconds to minutes and can range from an impaired consciousness, automatic movement, up to severe convulsions of the entire body. This contributes to a severe reduction in the quality of life and psychosocial functioning. Therefore, the unpredictable nature of seizures can be life-threatening, with a mortality rate in these patients which is 2-3 times higher than in the general population [4]. Impaired consciousness may lead to driving accidents, drowning, as well as to other serious injuries [5]. In particular, the most severe seizures, particularly when occurring at night, can result in sudden unexpected death in epilepsy (SUDEP) [6]. Epilepsy-related causes of death account for 40% of mortality in persons with epilepsy. In order to reduce morbidity and mortality due to epilepsy, real-time patient monitoring is essential for alerting family members and caregivers to administer prompt emergency medication and assist a person at the time of a seizure.

In the medical community, the standard procedures commonly used for epileptic patient monitoring are performed based on the video-EEG (v-EEG) [7]. v-EEG takes place in hospitals over several days and it involves the acquisition of the audio signal using a microphone, a video recording of a patient using a camera, the brain electrical activity using electroencephalography (EEG), as well as electrocardiography (ECG). Considering the unpredictability of seizures, it is not possible to monitor patients on a long-term basis, due to the highly intrusive nature of these procedures.

With the currently flourishing era of embedded computing, wearable technologies are opening up new opportunities for real-time epileptic seizures monitoring. These new ultra-low-energy portable devices overcome the limitation of medical equipment for real-time and long-term patient monitoring. In particular, the portability of these devices allows real-time remote patient monitoring on a daily basis. Ambulatory real-time patient monitoring allows hospital physicians to access patient information remotely and, hence, prevent further patient state deterioration by early detection of epileptic seizures.

The most popular wearable system for epileptic seizure detection requires the use of EEG head caps with embedded electrodes for measuring brain's electrical activity [8]. The placement of electrodes is based on the international 10-20 system [9], [10]. In [11], a new scheme for epileptic seizure detection based on approximate entropy and discrete wavelet transform analysis of 100 EEG channels has been proposed. Furthermore, different approaches that use artificial neural networks for epileptic seizure detection based on EEG signals are reported in the literature. Nevertheless, all these methods use EEG head caps that are cumbersome and uncomfortable as they require from 23 to 256 wired electrodes to be placed on the patient's scalp. The majority of epileptic patients refuse to wear these caps due to negative effect of social stigma they are facing in their daily lives [12].

In order to alleviate the negative impact of social stigma on patient's daily life, several studies have been conducted to reduce the number of EEG electrodes needed for epileptic seizure detection. For instance, in [13], the authors use two different montages with reduced number of electrodes for automatic multimodal detection of epileptic seizures: eight electrodes in forehead montage, and seven electrodes in posterior montage. However, the proposed solution is still intrusive and, hence, the problem of social stigma persists.

It is an aim of the present invention to address problems known from prior art, and offer a less intrusive solution for real-time epileptic seizure detection.

SUMMARY OF INVENTION

In a first aspect, the invention provides a wearable system for epileptic seizure detection, comprising an eyeglasses frame, with a left arm and a right arm configured to rest over the ears of an intended person wearing the eyeglasses, a first pair of electrodes located in the left arm, and a second pair of electrodes located in the right arm, the first pair of electrodes and the second pair of electrodes arranged such to be in contact with the skull of the intended person wearing the eyeglasses, and an EEG signal acquiring system integral to the left and right arms, connected to measuring outputs of the respective first pair and second pair of electrodes.

In a preferred embodiment, the acquiring system comprises sampling means to acquire signals at the measuring outputs, at least one sampling frequency in a determined range, a processor unit; a power source; a memory unit; a plurality of analog units; and a wireless communication emitter configured to emit a signal to a wireless communication receiver. The processor unit is programmed with a code to execute a feature extraction from the acquired signals; and a classification of the output from the feature extraction, based on Random Forest.

In a further preferred embodiment, the feature extraction comprises a preprocessing step of discrete wavelet transform on the acquired signals; a first calculation of nonlinear features from the preprocessed acquired signals for different values of input parameters; a second calculation of power features on the acquired signals.

In a second aspect, the invention provides a real-time hierarchical event-driven classifier configured to extend a battery lifetime of the wearable system. The classifier comprises a simple classifier and a full classifier, whereby the simple classifier considers only a determined number ($K_1$) of available features and is computationally efficient; and the full classifier considers an entire set of available features and is accurate, but computationally complex; whereby the full classifier is only invoked if the simple classifier cannot provide confident classification results based on a number of agreeing decision trees, thereby reducing the computational complexity and extending the battery lifetime while maintaining a high classification accuracy.

BRIEF DESCRIPTION OF THE FIGURES

The invention will be understood through the detailed description of preferred embodiments and in reference to the figures, wherein.

DETAILED DESCRIPTION OF PREFERRED EMBODIMENTS

I. Introduction

The present invention provides a device that the inventors have named e-Glass, and generally comprises a wearable ultra-low energy system that uses four EEG electrodes embedded and hidden in the temples of glasses for real-time epileptic seizure detection in children. However the real-time epileptic seizure detection device may also be adapted for use with adults. More precisely, the present invention provides 1. a real-time personalized high-accuracy wearable system for epileptic seizure detection in children;
2. validation on CHB-MIT database (Physionet.org [14]); and
3. an evaluation of energy consumption and battery lifetime of the e-Glass system.

The remainder of the present description is organized as follows.

In Section II, we propose the real-time system for epileptic seizure detection in children with a limited number of electrodes, according to a preferred embodiment of the invention.

An experimental setup along with the evaluation of energy efficiency and performance of the system are presented in Section III.

In Section IV, we conclude that the proposed system monitors epileptic seizures in children with high classification performance and limited number of EEG electrodes on a long basis.

II. Real-Time Methodology for Epileptic Seizure Detection

Figure 1:
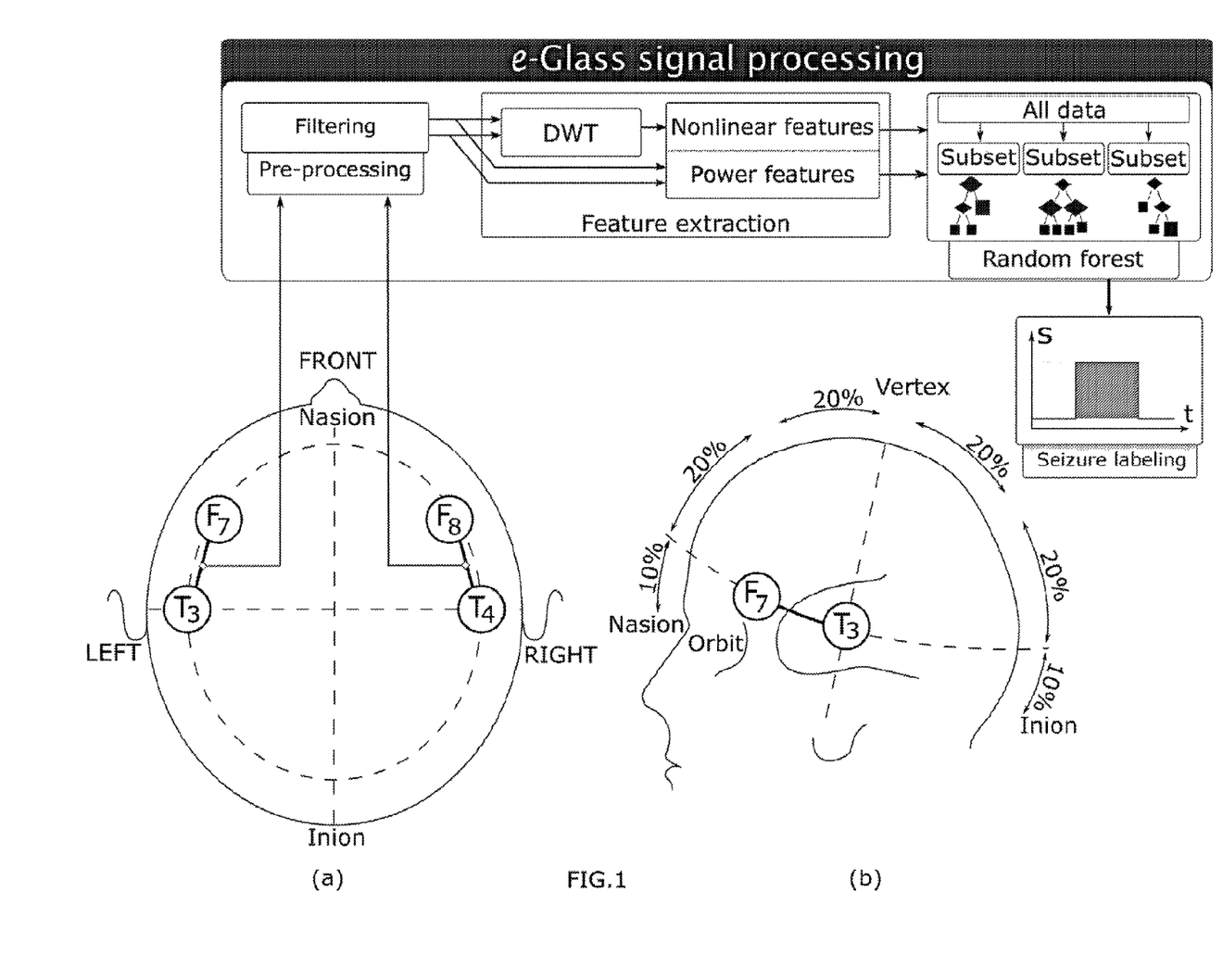
FIG. 1 shows an e-Glass wearable system for epileptic seizure detection according to an example embodiment of the invention.

In this section, we provide a detailed description of a preferred embodiment of the e-Glass product, the real-time wearable system for epileptic seizure detection in children. The overall flow of the proposed methodology is shown in FIG. 1 and it consists of three main phases: pre-processing (Section II-A), feature extraction (Section II-B), and classification (Section II-C). Each of these steps is thoroughly explained in the following subsections.

FIG. 1 at the lower left illustrates a generic head of a person seen in a view from above in (a) and in a side view in (b). On each of the left (a) and right (b) side of the head, 2 electrodes are positioned, i.e., electrodes T3 and F7 on the left side and T4 and F8 on the right side of the head. EEG signals are measured from the electrodes and output to a signal processing system, referenced as e-Glass signal processing in FIG. 1. The signal processing system performs for example 3 processing steps, which are described in more detail herein below, to finally output a Seizure Labeling as illustrated by the box in the lower right of FIG. 1.

A. Pre-Processing

The pre-processing step is optional, and represented by box 2 labeled filtering in FIG. 1.

EEG signals are often contaminated with different noise sources. The most common ones include the power line interference (50 or 60 Hz), the electrooculogram (EOG), and the electromyogram (EMG)—all 3 not represented in FIG. 1. Hence, we may first filter the EEG signals to remove the aforementioned artifacts.

B. Feature Extraction

The feature extraction step is illustrated by the central positioned box in FIG. 1 and receives at its input either the output from the optional pre-processing—this is as shown in FIG. 1—or directly from the electrodes positioned on the head.

Considering the complex, non-stationary, and nonlinear nature of EEG we extract various entropy measures to capture the nonlinear behavior of EEG signals, as well as several power features.

1) Nonlinear Features Extraction: when using entropy measures for epileptic seizure detection, it has been shown that applying a discrete wavelet transform (DWT) as a preprocessing step improves the detection rate for more than 20% [11]. Therefore, we decompose EEG signals down to level seven using a DWT. In particular, we use Daubechies 4 (db4) wavelet basis function (not shown in FIG. 1). The sample entropy values are calculated from the detail wavelet coefficients obtained at level 6 and 7—It is related to the DWT. Basically, the level refers to the number of times we filtered our signals. Further information may be found at www.mathworks.com/help/wavelet/ref/detcoef "D=detcoef (C,L,N) extracts the detail coefficients at level N from the wavelet decomposition structure [C,L]"—whereas the rest of the nonlinear features are calculated from detail wavelet coefficients at levels 3, 4, 5, 6, and 7 for different values of input parameters. We use the sample entropy [15], the permutation entropy [16], the renyi entropy [17], the shannon entropy [17], as well as the tsallis entropy [17]. In case of sample entropy these parameters are the dimension of sample entropy (we use dimension=2), as well as the tolerance (we use r standard deviation of a signal), where r={0.2, 0.35}.

In case of permutation entropy the parameters are again the dimension of permutation entropy (we use different dimensions dimension={3, 5, 7}) as well as the time lag (we use the time lag=1)).

In case of shannon, renyi and tsallis entropy we use q=2 (this parameter is called entropic-index).

2) Power features: epileptic seizures affect the distribution of EEG signal power in different frequency bands [18], [19]. The most commonly reported features extracted from EEG signals in the literature [20] rely on the averaged spectral power of EEG signals in various frequency bands of the EEG, namely delta [0.5,4] Hz, theta [4,8] Hz, alpha [8,12]

Hz, beta [13,30] Hz, gamma [30,45] Hz. We calculate the total EEG signal power along with the relative average powers of the EEG signal in the aforementioned frequency bands, as well as relative EEG powers in the following bands: [0,0.1] Hz, [0.1,0.5] Hz, [12,13] Hz. We use a modified periodogram to determine the average signal power in a specific band. These power features are extracted from raw EEG signals (not shown in FIG. 1).

C. Classification Based on Random Forest

The classification part is illustrated in the upper right box labelled random forest of FIG. 1.

Random forest generates an ensemble of decision trees that are combined to produce an aggregate mode, which is more powerful than any of its individual decision trees alone [21]. However, one of the main disadvantages of using a single decision tree for classification purposes is its overfitting tendency. Nonetheless, combining different decision trees into an ensemble solves the problem of overfitting.

Each of the classification trees is constructed using a bootstrap sample of data (not shown in FIG. 1). In particular, if our training set has M rows in the feature matrix, a bootstrap sample of data of size M is constructed by randomly picking one of the M rows of the dataset with replacement; hence, allowing the same row to be selected multiple times. This process is repeated M times resulting in a bootstrap sample of size M. This sample has the same number of rows as the training set, with possibly some rows from the training dataset missing while others occurring multiple times, just due to the nature of the random selection with replacement.

For each of the bootstrap samples, we grow an unpruned tree (fully grown) [22]. At each node, we randomly select a subset of features and we choose the best split within this smaller subset.

To classify a new sample, each decision tree gives a classification decision. The forest chooses the classification decision that has the most votes among the other trees in the forest. Using bootstrap aggregation, as well as random feature selection for growing each tree individually, results in a low-variance model and a robust outcome, as shown in our experiments in Section III. The highest classification accuracy of our system is obtained by random forest. However, our system is not classifier-dependent, hence, any other state-of-the-art classification algorithm can be used as well.

D. Event-Driven Classification Technique

Figure 6:
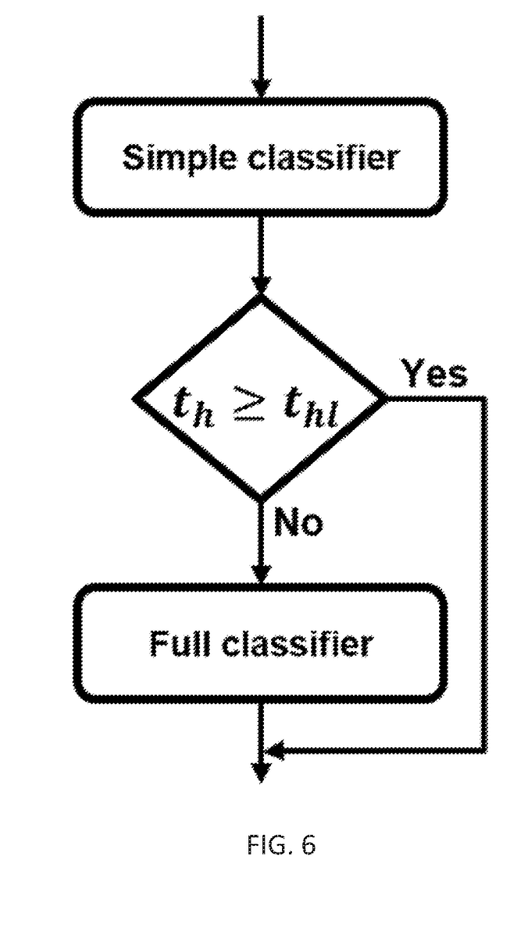
FIG. 6 shows the overall flow of our real-time hierarchical event-driven classification technique.

In an event-driven classification scheme, very often confident classification decisions can be made based on a subset of available features [43]. Therefore, we use a hierarchical event-driven classification technique that incorporates two random forest classifiers, as shown in FIG. 6. Namely, the simple classifier considers only $K_1$ features and is computationally efficient, but it cannot reach a high classification accuracy. On the other hand, the full classifier uses the entire set of available features and is very accurate, but computationally complex. Thus, we combine the benefits of these two classifiers, i.e., the low computational complexity of the simple classifier and the high classification accuracy of the full one. Our hierarchical event-driven classification technique maintains a high classification accuracy, while reducing the algorithm's computational complexity which, in turn, results in a longer battery lifetime of the e-Glass system.

In the training phase, we first extract the features from the input signals. Then, we sort these features according to their relevance. We assume that N is the total available number of features. The sample classifier considers only the first $K_1$ features, whereas the full classifier considers these $K_1$ features along with the other $N-K_1$ available features. We train both the sample and full classifier using the random forest algorithm. Both of these classifiers use the same number of trees within their respective forests.

Classification selection is done in the following way. First, we calculate the parameter $t_h$, which represents a percentage of mutually agreed trees. We define the confidence level of the sample classifier by comparing the value of the parameter $t_h$ to the value of the decision-making threshold set in the design phase $t_{ht}$, in order to decide which classifier is invoked.

In the testing phase, we first calculate the features from the simple classifier. We inspect the classification decision of each tree within the forest of the simple classifier and we calculate the parameter $t_h$. If the value of the parameter $t_h$ is above the decision-making threshold $t_{ht}$, i.e., if the simple classifier can make a confident decision based on its features, we take its classification decision as the final one. On the other hand, if no confident decision can be made using the simple classifier, we keep its $K_1$ features, and we calculate the rest of the $N-K_1$ available features. In this case, the final decision is that of the full classifier.

III. Experimental Setup and Results

In this section, we demonstrate the performance of our technique using the Physionet.org CHB-MIT Scalp EEG database. This database is described in Subsection III-A. Then, the target computing system of the e-Glass wearable platform on which we port our classification technique is explained in Subsection III-B. Next, the performance of our real-time detection algorithm is shown in Subsection III-C, and the energy consumption estimation is presented in Subsection III-D.

A. CHB-MIT Database

The used database contains EEG signals from children with refractory seizures. All recordings are collected from children (5 males, ages 3-22; and 17 females, ages 1.5-19). EEG signals are sampled at fs=256 Hz. The full database contains 24 subjects, with 198 seizures. In order to be able to evaluate the performance of the system according to the invention and the impact of the reduced number of electrodes, we consider multiple traces from 10 patients that are fully compliant with the standard acquisition protocol.

B. Target Platform

First Preferred Embodiment

Figure 2:
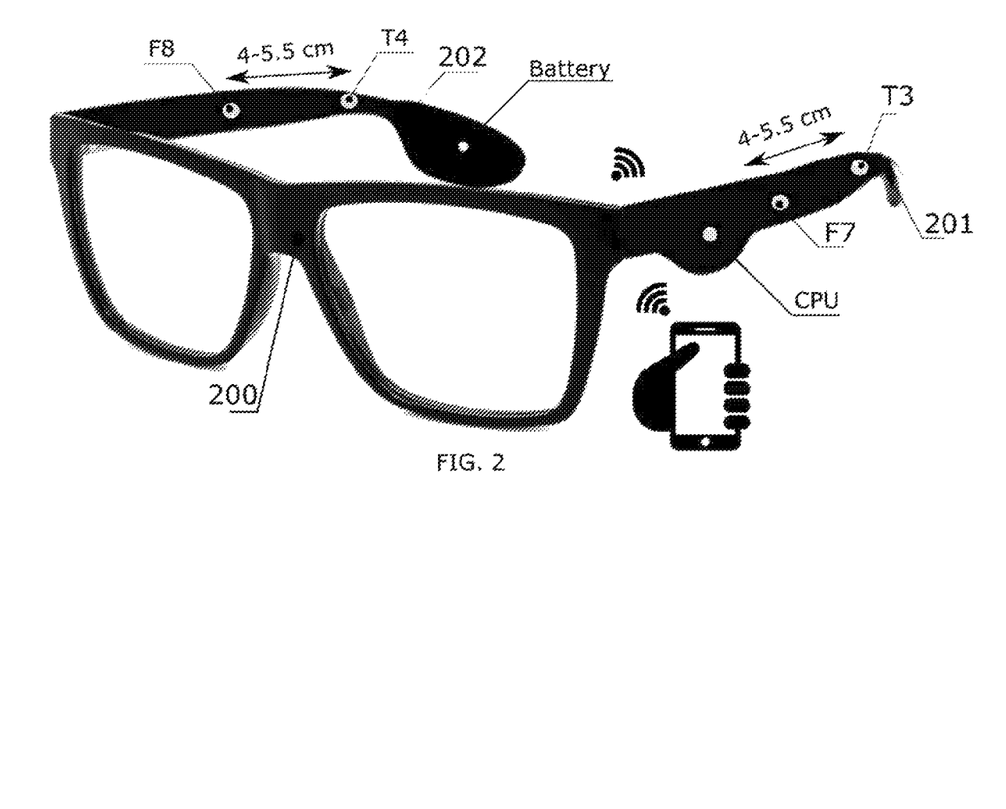
FIG. 2 shows a further example embodiment of the e-Glass wearable system according to the invention.

A first preferred embodiment of the inventive e-Glass wearable system is shown in FIG. 2. The system comprises an eyeglasses frame 200, with a left arm 201 and a right arm 202 configured to rest over the ears of an intended person wearing the eyeglasses (not shown in FIG. 2). The system acquires EEG signals from two electrode pairs: $F_7T_3$, and $F_8T_4$, shown in FIG. 1. The sampling frequency of acquired EEG signals ranges from 250 Hz up to 16 KHz with up to 24-bit resolution. Our device features an ultra-low power 32-bit microcontroller STM32L476 [23] with an ARM R Cortex R-M4 (labeled CPU in FIG. 2), which may operate at a maximum frequency of 80 MHz. e-Glass contains a 150 mAh battery (labeled Battery in FIG. 2), as well as 128 KB RAM, 512 KB Flash, and a 4-channel, low noise, 24-bit simultaneous-sampling Delta-Sigma ADC (not shown in FIG. 2). At the time of a seizure, a warning from e-Glass is sent to the caregivers (not shown in FIG. 2) through the communication with a mobile phone represented at the lower right of FIG. 2.

Second Preferred Embodiment

Figure 5:
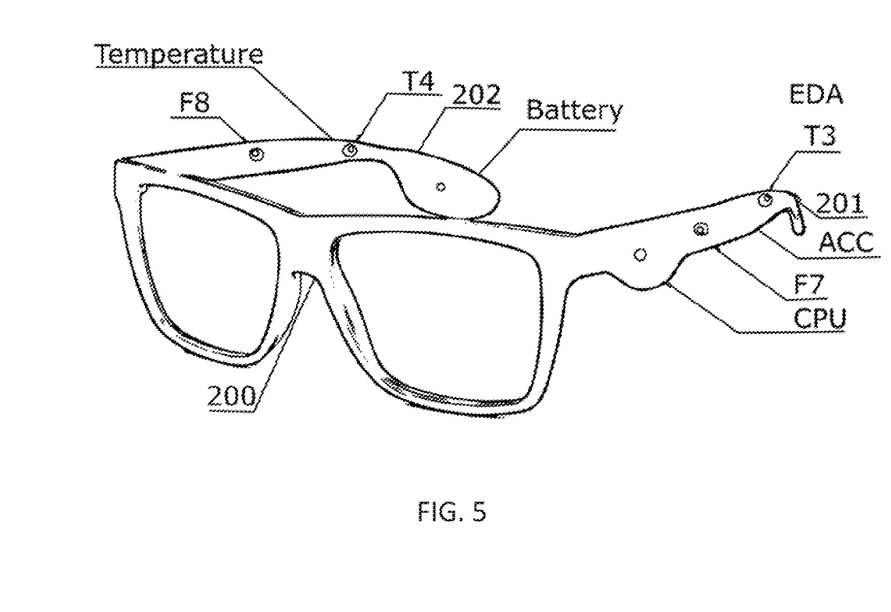
FIG. 5 shows an e-Glass wearable system according to a further example embodiment of the invention.

A second preferred embodiment of the e-Glass system is shown in FIG. 5. This embodiment comprises in addition an accelerometer sensor ACC, a temperature sensor "Temperature" and an electrodermal activity (EDA) sensor EDA. Each of the sensors in mounted in one of the left arm 201 or right arm 202. The manner in which they are mounted in FIG. 5 is to be considered as a possible example only.

Electrodes

One important criterion for the selection of EEG electrodes, e.g., electrodes $F_7$, $F_8$, $T_3$, and $T_4$, is the skin-electrode impedance. A low impedance contributes to the signal quality obtained during the acquisition in case of noise and motion artifact. Our system can use the following types of electrodes:

Gel electrodes—Conventional Ag/AgCl electrodes are used as the golden standard for the EEG signal acquisition. Namely, the top layer of the skin has a very high impedance [35]. The gel hydrates the top layer of the skin which lowers the skin-electrode impedance. During movement, the gel maintains the contact with the skin, reducing motion artifact. However, prior to using these electrodes, the skin preparation is recommended to improve the quality of EEG signals. This preparation is time-consuming and it requires an expert to position the electrodes on the scalp. Furthermore, the skin irritation is often reported during long-term measurements.

Dry electrode—Dry electrodes have larger skin-electrode impedance than the gel ones. We consider the following two types of these electrodes:

Hard dry electrodes—These electrodes are easier to be positioned on the scalp, as they do not involve the use of gel. In order to improve the signal-to-noise ratio (SNR), these electrodes are commonly used as active electrodes, which results in necessity of an extra hardware for signal amplification. In addition, some dry electrodes use microscale needles to reduce the skin-electrode impedance. However, this might cause skin irritation and infections [36].

Soft dry electrodes—Soft dry electrodes are based on soft polymers designed to provide better electrode-skin contact in comparison with the hard dry ones. Due to the absence of gel, these electrodes require similar patient preparation time as hard dry ones. Additionally, soft dry electrodes improve the signal quality and reduce skin irritation during long-term measurements [37].

Printed EEG electronic-tattoos—These dry electrodes are realized using screen-printing of carbon ink on a soft support. The direct contact of these electrodes with the skin results in high-quality signals along with high user comfort. Additionally, these electrodes use plasma polymerized 3,4-ethylenedioxythiophene to further improve the skin-electrode impedance [41].

Subcutaneous EEG electrodes—Subcutaneous signal acquisition results in higher quality signals in comparison with the one that uses surface electrodes, which in turns, reduces electric-noise and device-related artifacts. In case of long-term recordings, the signals quality does not change over time [42].

C. Performance Evaluation of Our Real-Time Detection Algorithm

1) Classification Performance Metric and Cross-Validation: We use the geometric mean of sensitivity and specificity (gmean) for inspecting the classifier's performance. These metrics are defined as follows:

$$\text{sensitivity} = \frac{tp}{tp + fn},$$

$$\text{specificity} = \frac{tn}{tn + fp},$$

$$gmean = \sqrt{\text{sensitivity} \cdot \text{specificity}},$$

where tp, tn, fp, fn represent the number of true positive, true negative, false positive, and false negative, respectively. We use gmean as it considers both sensitivity and specificity.

A sliding window of five seconds with a 80% overlap is used for extracting the features mentioned in Subsection II-B. Namely, we extract these features for both, seizure and seizure-free signal parts. In order to have balanced classes, the same number of seizure and seizure-free windows is used for each patient.

We split the data for each patient into training and test set. The training set contains 70% of randomly data, whereas the remaining 30% percent of data is used in the test set. This split is performed as follows. First we find the number of seizures for each patient. As we want to make sure that the test set contains at least one seizure, 30% of seizure data is put in the test set, whereas 70% goes to the training set. For instance, let us assume that patient A had 6 seizures. Then, feature windows that correspond to two seizures are put in the testing set, whereas the remaining four seizure windows are put in the training test. We use all possible combinations of six seizures to select two at a time for test set. For each split of seizure data, we perform the same approach for obtaining the training and test set for seizure-free data parts. The final results are averaged for each subject in our personalized approach.

2) Personalized Versus Generic: In this section, we investigate the difference in terms of classification performance between the personalized and generic approaches. Namely, the generic approach uses leave-one-out cross-validation scheme. Out of ten subjects, a single subject is retained for testing the model, and the remaining nine are used as training data. The personalized approach performs the classification based on the features extracted from different trials of one subject. Hence, this classification is done per subject. While splitting the data into training and test set, as explained in Subsection III-C, each trial is included into either the training set or the test set.

Figure 3:
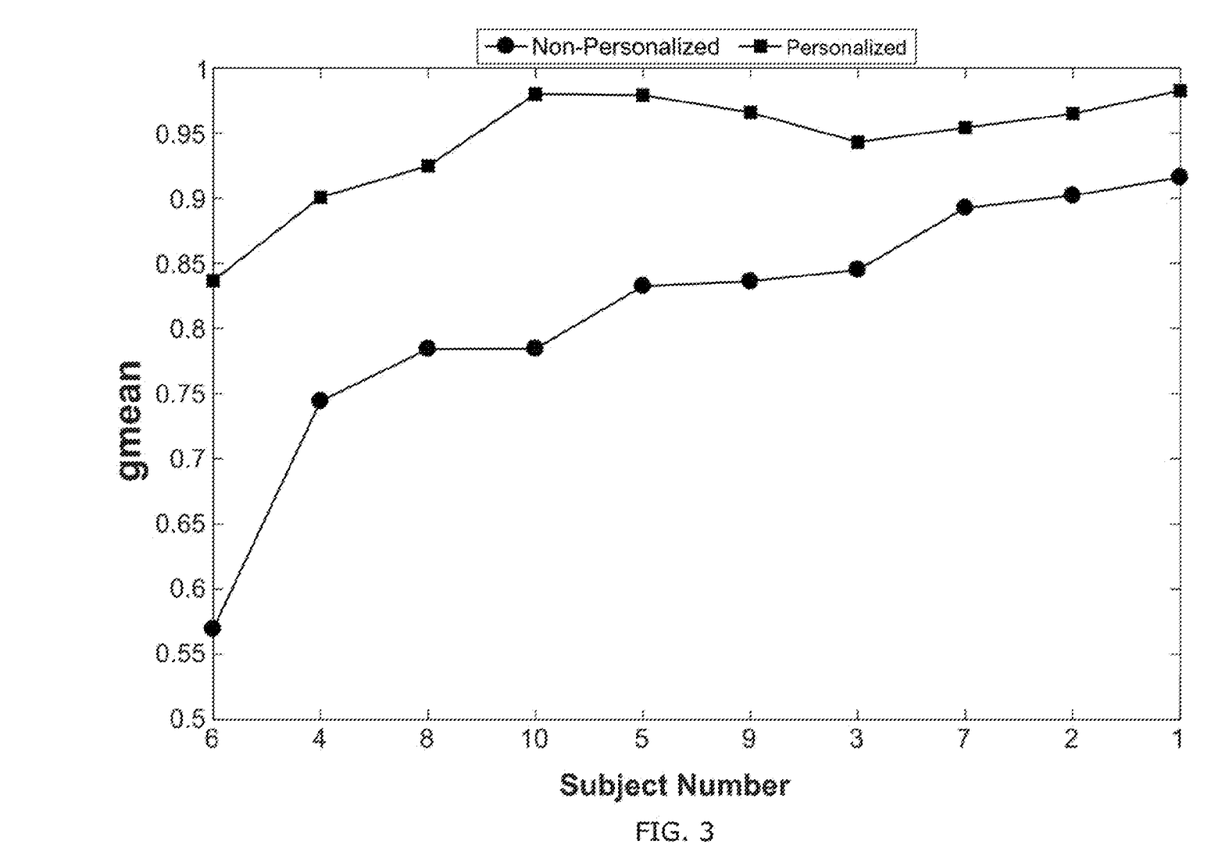
FIG. 3 contains a graph showing geometric mean (gmean) of sensitivity and specificity for personalized versus generic approach using four electrodes.

FIG. 3 shows the averaged gmean across all subjects (vertical axis) for four electrodes used: $F_7T_3$, and $F_8T_4$ in FIG. 1. The mean value across all subjects for the generic approach is 81.1%, whereas this value reaches 94.3% for the case of our personalized approach. In the best case, for patient 6 our approach improves the detection rate for 27%, as shown in FIG. 3. As we can infer from this figure, the personalized classification approach can adapt to significant inter-patient variations in EEG patterns. Thus, it achieves a higher classification accuracy.

Figure 4:
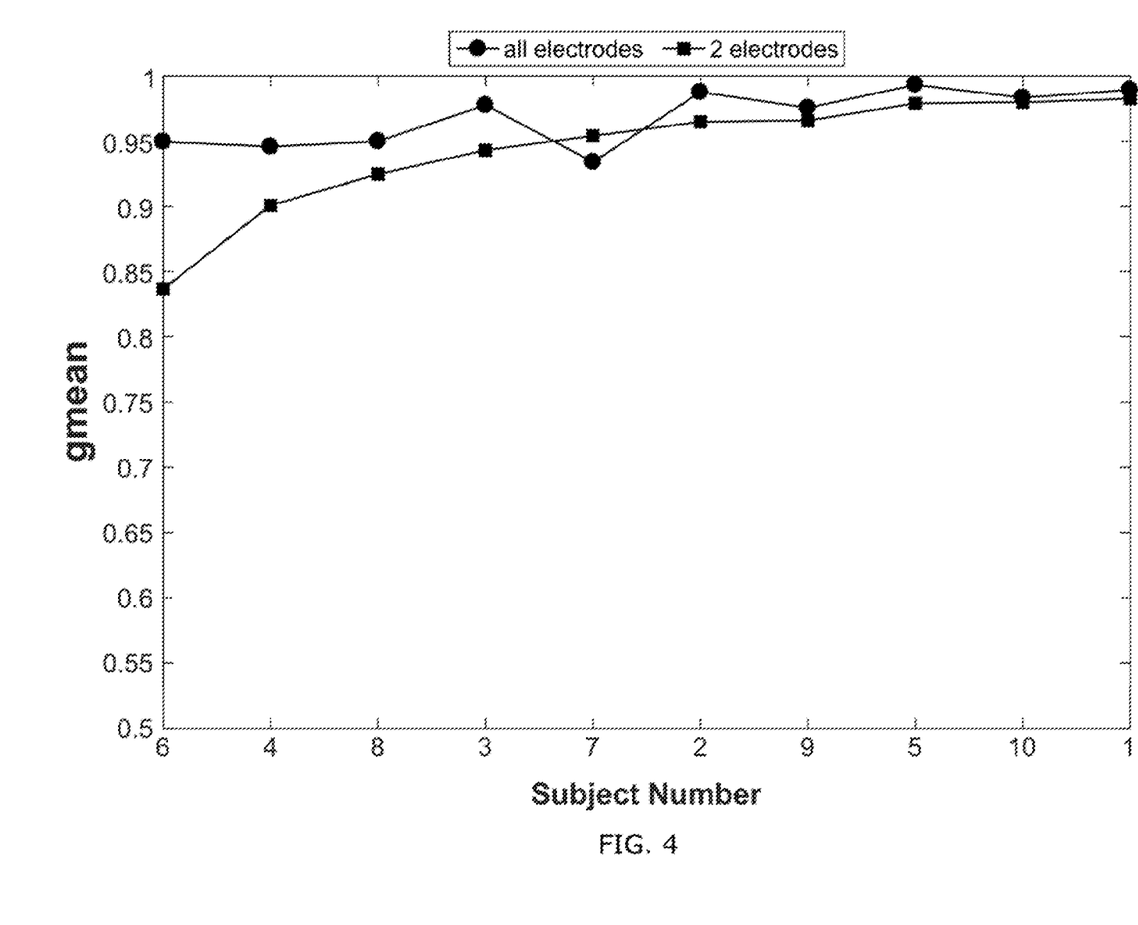
FIG. 4 contains a graph showing geometric mean (gmean) of sensitivity and specificity for personalized approach all electrodes versus four selected electrodes.

3) All EEG Electrodes Versus Reduced Set of Electrodes: In this section we compare the classification accuracy in case of the personalized approach for a different number of used electrodes. FIG. 4 shows gmean obtained for all available electrodes, as well as for the subset of four selected electrodes: $F_7T_3$, and $F_8T_4$. The average gmean value across all subjects is 97% and 94% for all electrodes and for the subset of electrodes, respectively. As it can be observed from FIG. 4, using only a few electrodes it is possible to ensure a high degree of wearability without any major loss in classification performance.

4) Full Classifier Versus Hierarchical Event-Driven Classification Technique: We fix the number of features in the simple classifier to $K_1=18$, whereas the full classifier considers a total number of $N=108$ features. By running the full classifier on the STM32L476 [23], we obtain that the execution time for processing a 4-second EEG window is equal to $t_{full}=447.6$ msecs, with the performance $G_{mean}=94.4\%$ On the other hand, the time it takes for our hierarchical event-driven classification technique to process this window is $t_{hierarchical}=99.9$ msecs, with $G_{mean}=94.5\%$. Therefore, our hierarchical classifier reduces the computational complexity by a factor of 4.48, while maintaining the same classification performance.

D. Energy Consumption

Our proposed e-Glass system includes a 150 mAh battery. Assuming that the EEG acquisition circuit is active all the time, we run our proposed real-time hierarchical event-driven classification technique every second detecting epileptic seizures from a four-second EEG window. The processing of a four-second window takes 99.9 msecs, resulting in 32.93 hours of operation on a single battery charge. Thus, it allows for 1.37 days of continuous operation.

All values for the preferred embodiment e-Glass are given as example only and may be varied according to required dimensioning, and as known by a person skilled in the art without departing from the invention.

Applications

The wearable system e-Glass may be used for different applications:

Emotional state assessment [24]—Using EEG signals to assess different music-induced emotional states (joy, anger, sadness, and pleasure) according to subject self-reported emotional states. Furthermore, EEG signals can be used in stress detection [32]. Moreover, monitoring of EDA offers the possibility to distinguish stress from cognitive load in an office environment [38]. Additionally, the variation in skin temperature is also used as another effective indicator of emotional status [39].

Playing different video games using mind control [25]—Users can control the game using their mind. This is done by translating users' EEG signals into commands that can be read by the game controller.

Epileptic seizure detection [34]—Epileptic seizures are reflected onto different changes in the EEG signal morphology. The occurrence of seizures can be detected by analyzing different features extracted from EEG signals. These features are mostly based on the power spectrum and signal complexity. Seizures usually involve head movements [40] that can be detected using ACC.

Patient monitoring in acute ischemic stroke (AIS) [26]—Due to a high correlation between EEG recordings and cerebral blood flow level, monitoring EEG signals can be used as a tool for the MS severity monitoring.

Rehabilitation of patients with severe motor disabilities [27]—Different brain-computer interfaces allow patients with motion and speech disabilities to talk with their family members and caretakers.

Monitoring of patients suffering from Alzheimer's disease (AD) [5-6]—EEG signals are used for monitoring the evolution of AD over time. Namely, by examining the EEG signals of these patients it can be noticed that the complexity of EEG patterns is remarkably reduced. Furthermore, a power shift towards lower frequencies can also be used as a severity marker of this disease.

Sleep stage analysis [7-8]—The EEG signal analysis could provide an insight into patient sleep disorders. Furthermore, this analysis can also differentiate between Non-REM and REM sleep cycles.

Migraine monitoring [33]—Migraine is a neurovascular disorder that causes headaches, and it is usually accompanied by nausea, vomiting, and sensitivity to light and sound. Real-time monitoring of patients' EEG signals can be beneficial for alerting family members and caregivers to assist a person at the time of headache.

IV. Conclusions

The e-Glass, is a preferred embodiment according to the invention of a new wearable device for real-time epileptic seizure detection in children. The experimental evaluation demonstrates that the personalized approach provided by the use of e-Glass outperforms the generic approach in terms of classification accuracy. Furthermore, it also ensures the high degree of wearability without any major loss in terms of classification performance. This reduced set of electrodes overcomes the lack of portability of hospital equipment, as well as it reduces the computational complexity, which further leads to a reduction in energy consumption. Thus, e-Glass may provide an early warning of epileptic seizures and promptly inform patient family members of preventive measures to avoid epilepsy-related death or possible accidents during seizures. Overall, e-Glass may significantly contribute to improvements in quality of life, as well as reducing socioeconomic burden of epilepsy.

REFERENCES

[1] M. Patricia O. Shafer, R N, "About Epilepsy: The Basics—Epilepsy Foundation," pp. 4-5, 2014. [Online]. Available: https://www.epilepsy.com/learn/about-epilepsy-basics

[2] D. Hirtz, D. J. Thurman, K. Gwinn-Hardy, M. Mohamed, A. R. Chaudhuri, and R. Zalutsky, "How common are the "common" neurologic disorders?" Neurology, vol. 68, no. 5, pp. 326-337, January 2007.

[3] P. Kwan and M. J. Brodie, "Definition of refractory epilepsy: defining the indefinable?" The Lancet. Neurology, vol. 9, no. 1, pp. 27-9, January 2010.

[4] A. e. a. Szucs, "Sudden death and mortality in epilepsy." vol. 59, no. 9-10, pp. 321-8, September 2006.

[5] H. Blumenfeld, "Impaired consciousness in epilepsy." The Lancet. Neurology, vol. 11, no. 9, pp. 814-26, September 2012.

[6] P. Ryvlin, T. Tomson, and A. Montavont, "[Excess mortality and sudden unexpected death in epilepsy]." Presse medicale (Paris, France: 1983), vol. 38, no. 6, pp. 905-10, June 2009.

[7] G. D. Cascino, "Video-EEG Monitoring in Adults," Epilepsia, vol. 43, no. s3, pp. 80-93, June 2002.

[8] J. Blom and M. Anneveldt, "An electrode cap tested," Electroencephalography and Clinical Neurophysiology, vol. 54, no. 5, pp. 591-594, November 1982.

[9] "10-20 system (EEG)—an overview—ScienceDirect Topics."

[10] "10/20 System Electrode Distances—DIY tDCS." [Online]. Available: https://www.diytdcs.com/2012/07/1020-system-electrode-distances/[11]

[11] H. Ocak, "Automatic detection of epileptic seizures in EEG using discrete wavelet transform and approximate entropy," Expert Systems with Applications, vol. 36, no. 2, pp. 2027-2036, mar 2009.

[12] C. Hoppe, M. Feldmann, B. Blachut, R. Surges, C. E. Elger, and C. Helmstaedter, "Novel techniques for automated seizure registration: Patients' wants and needs," Epilepsy & Behavior, vol. 52, no. Pt A, pp. 1-7, November 2015.

[13] F. Furbass, S. Kampusch, E. Kaniusas, J. Koren, S. Pirker, R. Hopfengartner, H. Stefan, T. Kluge, and C. Baumgartner, "Automatic multimodal detection for long-term seizure documentation in epilepsy," Clinical Neurophysiology, vol. 128, no. 8, pp. 1466-1472, August 2017.

[14] A. L. Goldberger, L. A. Amaral, L. Glass, J. M. Hausdorff, P. C. Ivanov, R. G. Mark, J. E. Mietus, G. B. Moody, C. K. Peng, and H. E. Stanley, "PhysioBank, PhysioToolkit, and PhysioNet: components of a new research resource for complex physiologic signals." Circulation, vol. 101, no. 23, pp. E215-20, June 2000.

[15] X. Xinnian Chen, I. Solomon, and K. Chon, "Comparison of the Use of Approximate Entropy and Sample Entropy: Applications to Neural Respiratory Signal," in 2005 IEEE Engineering in Medicine and Biology 27th Annual Conference, vol. 4. IEEE, 2005, pp. 4212-4215.

[16] C. Bandt and B. Pompe, "Permutation Entropy: A Natural Complexity Measure for Time Series," Physical Review Letters, vol. 88, no. 17, p. 174102, April 2002.

[17] U. R. Acharya, H. Fujita, V. K. Sudarshan, S. Bhat, and J. E. Koh, "Application of entropies for automated diagnosis of epilepsy using EEG signals: A review," Knowledge-Based Systems, vol. 88, pp. 85-96, 2015.

[18] A. Sharma, "Epileptic seizure prediction using power analysis in beta band of EEG signals," in 2015 International Conference on Soft Computing Techniques and Implementations (ICSCTI). IEEE, October 2015, pp. 117-121.

[19] "A closer look at EEG—Epilepsy Society." [Online]. Available: https://www.epilepsysociety.org.uk/closer-look-eeg#.WhE8o7aZPxg

[20] M. A. Bell and K. Cuevas, "Using EEG to Study Cognitive Development: Issues and Practices." Journal of cognition and development: official journal of the Cognitive Development Society, vol. 13, no. 3, pp. 281-294, July 2012.

[21] R. Diaz-Uriarte and S. A. de Andres, "Gene selection and classification of microarray data using random forest," BMC Bioinformatics, vol. 7, p. 3, 2006.

[22] A. Liaw and M. Wiener, "Classification and regression by randomforest," R News, vol. 2, no. 3, pp. 18-22, 2002.

[23] "STM32L1 Series—STMicroelectronics."

[24] Y.-P. Lin, C.-H. Wang, T.-P. Jung, T.-L. Wu, S.-K. Jeng, J.-R. Duann, and J.-H. Chen, "Eeg-based emotion recognition in music listening", IEEE Transactions on Biomedical Engineering, vol. 57, no. 7, pp. 1798-1806, 2010.

[25] "Eeg games top 5 list: Playing with your brainwaves," The MindWave Headset: Making EEG Games Possible, 2018. [Online]. Available: http: //neurosky.com/2015/09/eeg-games-top-5-list-playing-with-your-brainwaves/[26]

[26] K. G. Jordan, "Emergency eeg and continuous eeg monitoring in acute ischemic stroke", Journal of Clinical Neurophysiology, vol. 21, no. 5, pp. 341-352, 2004.

[27] J. J. Daly and J. R. Wolpaw, "Brain-computer interfaces in neurological rehabilitation," The Lancet Neurology, vol. 7, no. 11, pp. 1032-1043, 2008.

[28] L. A. Coben, W. Danziger, and M. Storandt, "A longitudinal eeg study of mild senile dementia of alzheimer type: changes at 1 year and at 2.5 years", Electroencephalography and clinical neurophysiology, vol. 61, no. 2, pp. 101-112, 1985.

[29] J. Jeong, "Eeg dynamics in patients with alzheimer's disease", Clinical neurophysiology, vol. 115, no. 7, pp. 1490-1505, 2004.

[30] D. J. Dijk, D. G. M. Beersma, G. M. Bloem; Sex Differences in the Sleep EEG of Young Adults: Visual Scoring and Spectral Analysis, Sleep, vol. 12, pp. 500-507, 1989.

[31] R. Boostani, F. Karimzadeh, M. Nami; "A comparative review on sleep stage classification methods in patients and healthy individuals", vol. 140, pp. 77-91, 2017.

[32] S. A. Hosseini and M. A. Khalilzadeh, "Emotional Stress Recognition System Using EEG and Psychophysiological Signals: Using New Labelling Process of EEG Signals in Emotional Stress State", pp. 1-6, 2010.

[33] R. Bellotti, F. De Carlo, M. de Tommaso and M. Lucente, "Migraine detection through spontaneous EEG analysis", pp. 1834-1837, 2007.

[34] S. Ramgopal et al., "Seizure detection, seizure prediction, and closed-loop warning systems in epilepsy", vol. 37, pp. 291-337, 2014.

[35] Webster, J. G.; Clark, J. W. Medical Instrumentation: Application and Design; Wiley: Noboken, 2008.

[36] Y. H. Chen et al., "Soft, Comfortable Polymer Dry Electrodes for High Quality ECG and EEG Recording", vol. 14, pp. 23758-23780, 2014.

[37] F. Stauffer et al., "Skin Conformal Polymer Electrodes for Clinical ECG and EEG Recordings", vol. 7, 2018.

[38] C. Setz et al., "Discriminating Stress From Cognitive Load Using a Wearable EDA Device", vol. 14, pp. 410-417, 2010.

[39] K. Kim, S. Bang, S. Kim, "Emotion recognition system using short-term monitoring of physiological systems", vol. 42, pp. 419-427, 2004.

[40] R. O'Dwyer et al., "Lateralizing Significance of Quantitative Analysis of Head Movements before Secondary Generalization of Seizures of Patients with Temporal Lobe Epilepsy", vol. 48, pp. 524-530, 2007.

[41] L. Bareket et al., "Temporary-tattoo for long-term high fidelity biopotential recordings", vol. 6, 2016.

[42] J. Duun-Henriksen et al., "EEG Signal Quality of a Subcutaneous Recording System Compared to Standard Surface Electrodes", vol. 2015, pp. 1-9, 2015.

[43] Sopic, Dionisije, Amin Aminifar, Amir Aminifar, and David Atienza. "Real-Time Event-Driven Classification Technique for Early Detection and Prevention of Myocardial Infarction on Wearable Systems." *IEEE transactions on biomedical circuits and systems* 99 (2018): 1-11

The invention claimed is:

1. A wearable system for real-time detection of epileptic seizure based on electroencephalography, comprising:
an eyeglass frame comprising first and second arms, each arm configured to rest over a respective ear of a user of the eyeglass frame;
first and second head electrodes supported by the first arm, and third and fourth head electrodes supported by the second arm;
wherein the first and second head electrodes are respectively located at arm positions corresponding to head positions T3 and F7, and the third and fourth head electrodes are respectively located at arm positions corresponding to head positions T4 and F8, so that the system only has these four head electrodes, and no additional head electrodes, for detecting epileptic seizures, the first, second, third and fourth head electrodes configured to be in contact with a head of the user for detecting epileptic seizures; and a processor, comprising processing circuitry, connected to measuring outputs of the first, second, third, and fourth electrodes, and configured to:

detect seizures of the user based on signals from the first, second, third and fourth electrodes processed via a hierarchical system comprising a simple classifier and a full classifier, wherein the simple classifier is configured to consider a determined number ($K_1$) of available features from the electrodes and is computationally efficient, and the full classifier is configured to consider an entire set of the available features from the electrodes and is accurate but computationally complex, and wherein the full classifier is configured to be invoked when the simple classifier cannot provide sufficient classification results based on a number of agreeing decision trees to reduce the computational complexity and extending the battery lifetime while providing a high classification accuracy for detecting seizures.

2. The wearable system of claim 1, wherein the processor is configured to use a 24-bit resolution sampling mean configured to measure analog signals from the first, second, third, and fourth electrodes, and to control to emit a signal to a wireless communication receiver via an emitter.

3. The wearable system of claim 1, wherein the processor is configured to perform feature extraction comprising:

a preprocessing step of discrete wavelet transform on acquired signals from the electrodes;

a first calculation of nonlinear features from the preprocessed acquired signals for different input parameters; and a second calculation of power features on the acquired signals.

4. The wearable system of claim 1, wherein the simple classifier and the complex classifier are trained via a random forest algorithm, and are random forest classifiers.

5. The wearable system of claim 4, wherein the simple classifier and the complex classifier are configured to use the same number of trees within their respective forests.

6. The wearable system of claim 1, wherein the processor is configured to compare values to determine whether to invoke the simple classifier or the full classifier.

7. A method of using a wearable system for real-time detection of epileptic seizure based on electroencephalography, the method comprising:

having an eyeglass frame comprising first and second arms, each arm configured to rest over a respective ear of a user of the eyeglass frame;

wherein the eyeglass frame comprises first and second head electrodes supported by the first arm, and third and fourth head electrodes supported by the second arm;

wherein the first and second head electrodes are respectively located at arm positions corresponding to head positions T3 and F7, and the third and fourth head electrodes are respectively located at arm positions corresponding to head positions T4 and F8, for detecting epileptic seizures, the first, second, third and fourth head electrodes configured to be in contact with a head of the user for detecting epileptic seizures, so that the system only has these four head electrodes for detecting epileptic seizures; and measuring and using outputs of the first, second, third, and fourth electrodes to detect seizures via a hierarchical system comprising a simple classifier and a full classifier, wherein the simple classifier considers a determined number ($K_1$) of available features from the electrodes and is computationally efficient, and the full classifier considers an entire set of available features from the electrodes and is accurate but more computationally complex than is the simple classifier, and comparing values to determine whether to invoke the simple classifier or the full classifier, comprising invoking the full classifier when the simple classifier cannot provide sufficient classification results based on a number of agreeing decision trees to reduce the computational complexity and extending the battery lifetime while providing a high classification accuracy for detecting seizures.

8. The method of claim 7, further comprising using a 24-bit resolution sampling mean to measure analog signals from the first, second, third, and fourth electrodes, and emitting wireless signals to a wireless communication receiver via an emitter.

9. The method of claim 7, further comprising training the simple classifier and the complex classifier via a random forest algorithm.

10. The method of claim 9, wherein the simple classifier and the complex classifier use the same number of trees within their respective forests.

11. The method of claim 7, further comprising performing feature extraction comprising:

a preprocessing step of discrete wavelet transform on acquired signals from the electrodes;

a first calculation of nonlinear features from the preprocessed acquired signals for different input parameters; and a second calculation of power features on the acquired signals.

\* \* \* \* \*